United States Patent
Blenke et al.

(10) Patent No.: US 6,746,437 B2
(45) Date of Patent: Jun. 8, 2004

(54) ABSORBENT ARTICLE CONTAINMENT LINER AND ASSEMBLY THEREOF

(75) Inventors: Timothy J. Blenke, Neenah, WI (US); Julie A. Moser, Lawrenceburg, IN (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 65 days.

(21) Appl. No.: 10/080,774

(22) Filed: Feb. 22, 2002

(65) Prior Publication Data

US 2002/0077616 A1 Jun. 20, 2002

Related U.S. Application Data

(63) Continuation of application No. 09/429,207, filed on Oct. 28, 1999, now Pat. No. 6,436,079.

(51) Int. Cl.[7] .................................................. A61F 13/15
(52) U.S. Cl. ............................ 604/385.19; 604/385.24
(58) Field of Search ................... 604/385.01, 385.08, 604/385.19, 385.21, 385.23, 385.24, 385.25, 385.27, 385.28, 385.101, 385.12

(56) References Cited

U.S. PATENT DOCUMENTS

| | | | | |
|---|---|---|---|---|
| 4,430,088 A | * | 2/1984 | Karami | 604/385.21 |
| 4,662,877 A | | 5/1987 | Williams | |
| 4,738,677 A | | 4/1988 | Foreman | |
| 4,753,646 A | | 6/1988 | Enloe | |
| 4,816,025 A | * | 3/1989 | Foreman | 604/385.27 |
| 4,892,536 A | | 1/1990 | DesMarais et al. | |
| 4,990,147 A | | 2/1991 | Freeland | |
| 5,026,364 A | | 6/1991 | Robertson | |
| 5,037,416 A | | 8/1991 | Allen et al. | |
| 5,269,775 A | | 12/1993 | Freeland et al. | |
| 5,304,159 A | * | 4/1994 | Tanji et al. | 604/385.19 |
| 5,304,160 A | | 4/1994 | Igaue et al. | |
| 5,344,516 A | | 9/1994 | Tanji et al. | |
| 5,397,318 A | | 3/1995 | Dreier | |
| 5,439,459 A | | 8/1995 | Tanji et al. | |
| 5,569,227 A | | 10/1996 | Vandemoortele et al. | |
| 5,593,401 A | * | 1/1997 | Sosalla et al. | 604/385.28 |
| 5,779,690 A | | 7/1998 | Gustafsson et al. | |
| 5,817,086 A | | 10/1998 | Kling | |
| 5,827,259 A | | 10/1998 | Laux et al. | |
| 5,938,652 A | | 8/1999 | Sauer | |
| 6,077,254 A | * | 6/2000 | Silwanowicz et al. | 604/385.21 |

FOREIGN PATENT DOCUMENTS

| | | |
|---|---|---|
| EP | 433 951 | 6/1991 |
| EP | 382 022 | 1/1994 |
| GB | 2 284 537 | 6/1995 |
| GB | 2 284 538 | 7/1997 |
| WO | 97/15260 | 5/1997 |

* cited by examiner

*Primary Examiner*—Weilun Lo
*Assistant Examiner*—C. Lynne Anderson
(74) *Attorney, Agent, or Firm*—Pauley Petersen & Erickson

(57) ABSTRACT

A containment liner assembly is provided having first and second elongated elasticized members and a containment liner member. The first and second elongated elasticized members are adapted to be disposed along first and second longitudinal sides of an absorbent article chassis, respectively, with a first end portion of each of the first and second elongated elasticized members coterminous with one of the front and back edges of the absorbent article. The containment liner member has opposed first and second ends with the first end joined with the first elongated elasticized member first end portion and the second end joined with the second elongated elasticized member first end portion. Also, provided are associated absorbent articles and methods for providing a containment liner to an absorbent article.

15 Claims, 3 Drawing Sheets

ABSORBENT ARTICLE CONTAINMENT LINER AND ASSEMBLY THEREOF

CROSS REFERENCE TO RELATED APPLICATION

This application is a continuation of patent application Ser. No. 09/429,207, filed on Oct. 28, 1999 now U.S. Pat. No. 6,436,079.

FIELD OF THE INVENTION

This invention relates generally to absorbent articles and, more particularly, to containment liner assemblies as well as corresponding absorbent articles and associated methods.

BACKGROUND OF THE INVENTION

A wide variety of types of structures are known in the art for use in or as absorbent articles, particularly disposable absorbent articles, used to collect various body fluids and exudates. Commercial forms or embodiments of such absorbent articles include diapers, adult incontinence products, sanitary napkins and bandages. Disposable products of these types generally comprise components for receiving, absorbing and retaining fluids. Typically, various of the components of such articles are in the form of a chassis which includes a liquid permeable topsheet, an absorbent core and a liquid impermeable backsheet.

Certain absorbent articles, such as the disposable absorbent articles commonly known as "diapers," are typically worn about the waist to collect and retain exudates, including fecal matter and urine, from the wearer. Disposable absorbent articles having elastic leg bands have become popular as the use of elastic around the legs of a wearer, e.g., a baby, tends to prevent leakage of such bodily exudates from the article. In practice, the topsheet of such disposable absorbent articles is commonly worn adjacent to the body of the wearer and desirably operates to permit the passage of at least certain fluid form bodily exudates therethrough to be retained by, in or near an underlying absorbent structure or core.

Unfortunately, solid wastes and exudates, such as fecal matter, may typically remain on the surface of such absorbent article topsheet and thus remain in contact with the skin of the wearer. As will be appreciated, it is generally desirable to avoid or minimize extensive contact of the skin of the wearer by or with such bodily exudates. To that end, certain developments in the art have been directed to isolating bodily exudates from the skin of the wearer. For example, disposable absorbent articles which include a topsheet with an opening or hole to allow fecal matter to pass through the topsheet have been developed. Certain of such disposable articles include a topsheet wherein the perimeter region of such opening or hole has been elasticized.

While such articles may be of some benefit in avoiding or minimizing extensive contact of the skin of the wearer by or with such bodily exudates, further improvements are generally desired. For example, there is a continuing need in the art for a containment assembly which properly addresses isolation of bodily exudates, such as fecal matter. In particular, there is a need that the absorbent articles provide a containment space of sufficient volume to properly provide desired isolation of fecal matter while maintaining the designed for absorbency properties or characteristics of the article. Further, there is a need and a demand for a containment assembly which desirably addresses such needs despite likely or possible differences in the anatomy of the wearer.

Still further, there is need and a demand for a containment liner assembly as well as corresponding absorbent articles and associated methods such as may be better suited for large scale manufacture and production.

SUMMARY OF THE INVENTION

A general object of the invention is to provide one or more improved containment liner assembly, absorbent article and associated methods.

A more specific objective of the invention is to overcome one or more of the problems described above.

The general object of the invention can be attained, at least in part, through an absorbent article including a front waist area forming a front edge, a back waist area forming a back edge and a crotch area disposed between the front and rear waist areas. The absorbent article has a chassis which includes an absorbent structure. The chassis also has opposed first and second longitudinal sides and opposed first and second lateral sides. The absorbent article includes:

a first elongated elasticized member disposed along the first longitudinal side of the chassis, a second elongated elasticized member disposed along the second longitudinal side of the chassis, wherein each of the first and second elongated elasticized members have a first end portion coterminous with one of the front and back edges, and a first containment liner member having opposed first and second ends with the first end joined with the first elongated elasticized member first end portion and the second end joined with the second elongated elasticized member first end portion.

The prior art generally fails to provide absorbent articles which avoid or minimize contact of the skin of the wearer by or with bodily exudates to the extent desired in many applications or uses. Further, the prior art generally fails to provide absorbent articles which afford a containment space of sufficient volume to properly provide desired isolation of fecal matter while maintaining the designed for absorbency properties or characteristics of the article. Still further, the prior art generally fails to provide a containment liner assembly as well as corresponding absorbent articles and associated methods such as are desirably suited for large scale manufacture and production.

The invention further comprehends a containment liner assembly for an absorbent article which includes a front waist area forming a front edge, a back waist area forming a back edge and a crotch area disposed between the front and rear waist areas. The absorbent article also has a chassis which includes an absorbent structure. The chassis has opposed first and second longitudinal sides and opposed first and second lateral sides.

A containment liner assembly, in accordance with one preferred embodiment of the invention, includes:

first and second elongated elasticized members adapted to be disposed along the first and second longitudinal sides of the chassis, respectively, with a first end portion of each of the first and second elongated elasticized members coterminous with one of the front and back edges, and a first containment liner member having opposed first and second ends with the first end joined with the first elongated elasticized member first end portion and the second end joined with the second elongated elasticized member first end portion.

The invention still further comprehends a method for providing a containment liner to an absorbent article having a front waist area forming a front edge, a back waist area forming a back edge and a crotch area disposed between the front and rear waist areas. The absorbent article also has a chassis which includes an absorbent structure. The chassis has opposed first and second longitudinal sides and opposed first and second lateral sides.

In accordance with one preferred embodiment of the invention, such a method includes:
    forming a containment liner assembly by,
        joining a first end of a first containment liner member with a first end portion of a first elongated elasticized member, and
        joining an opposed second end of the first containment liner member with a first end portion of a second elongated elasticized member, and
    joining the containment liner assembly with the chassis by,
        joining the first elongated elasticized member along the first longitudinal side of the chassis such that the first end portion of the first elongated elasticized member is coterminous with one of the front and back edges and
        joining the second elongated elasticized member along the second longitudinal side of the chassis such that the first end portion of the second elongated elasticized member is also coterminous with the one of the front and back edges with which the first end portion of the first elongated elasticized member is coterminous.

Other objects and advantages will be apparent to those skilled in the art from the following detailed description taken in conjunction with the appended claims and drawing.

DETAILED DESCRIPTION OF THE PRESENTLY PREFERRED EMBODIMENTS

The present invention provides improved containment liner assemblies as well as corresponding absorbent articles and associated methods.

Figure 1:
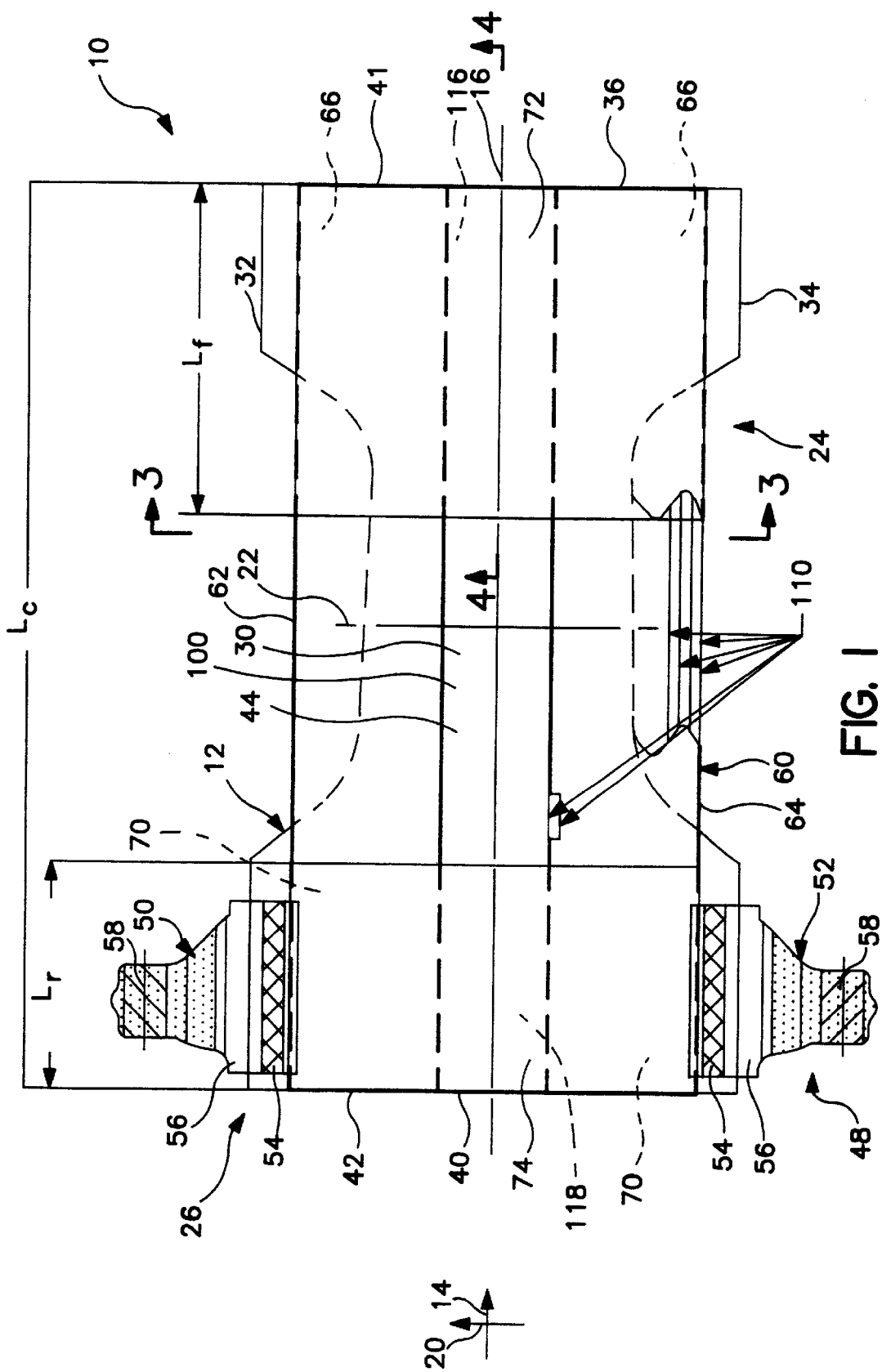
FIG. 1 is a partially cut-away top plan view of a disposable diaper absorbent article in accordance with one preferred embodiment of the invention in a flat-out, uncontracted state (i.e., with all elastic induced gathering and contraction removed).
Figure 3:
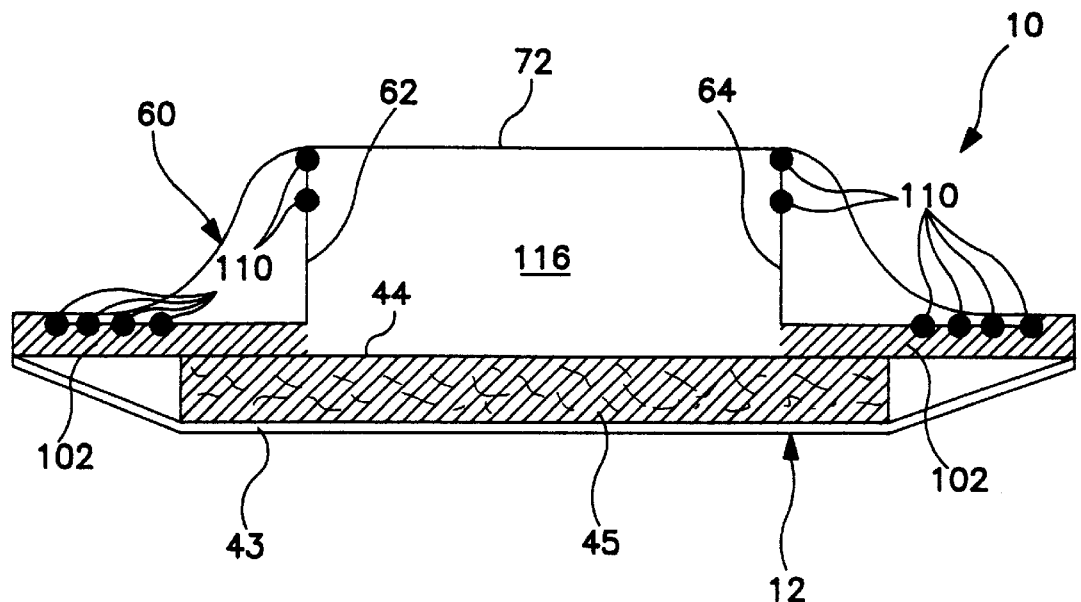
FIG. 3 is a simplified sectional view of the disposable diaper absorbent article shown in FIG. 1, taken substantially along the line 3—3 of FIG. 1 and viewed in the direction of the arrows.
Figure 4:
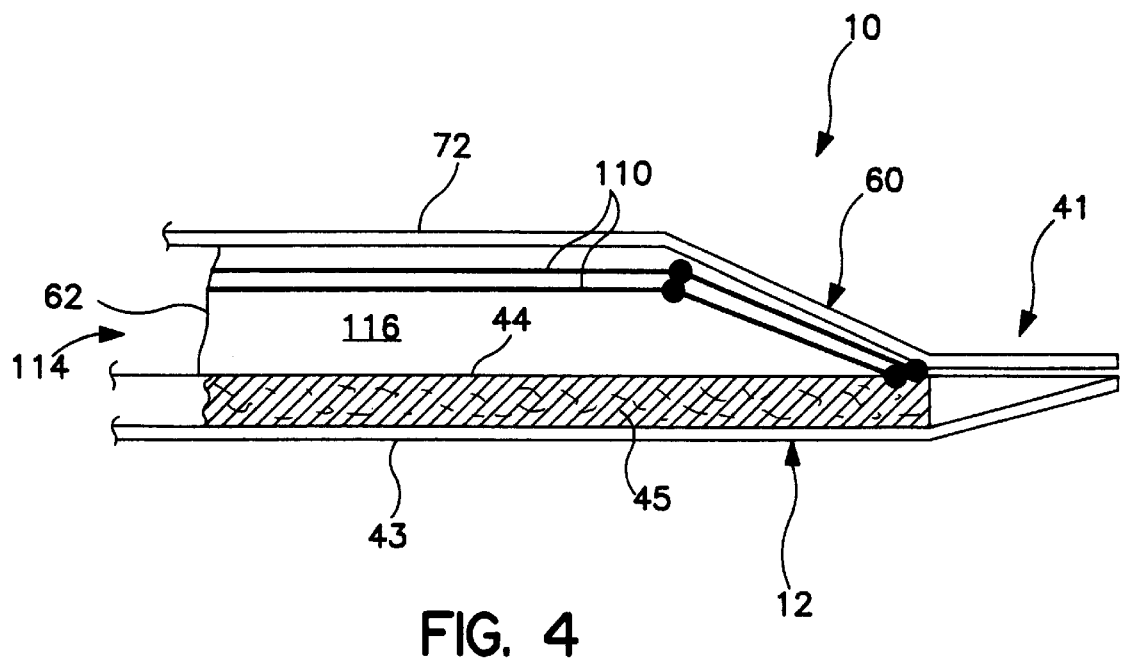
FIG. 4 is a simplified fragmentary sectional view of the disposable diaper absorbent article shown in FIG. 1, taken substantially along the line 4—4 of FIG. 1 and viewed in the direction of the arrows.

Referring initially to FIGS. 1, 3 and 4, there is illustrated an absorbent article, generally designated by the reference numeral 10, in accordance with one embodiment of the invention. As will be appreciated, the absorbent article 10 has the general form of a disposable diaper such as adapted to be worn about the lower torso by an infant. It is to be understood, however, that while the invention is described below with particular reference to disposable diapers, the broader practice of the invention is not necessarily so limited. For example, the invention can, if desired, be applied to other forms or types of absorbent articles including various disposable absorbent articles such as are generally configured to collect and contain human discharges or exudates such as, including, urine and fecal material and which articles also desirably avoid leakage of such discharge materials.

The diaper absorbent article 10 generally includes a chassis 12, such as generally known in the art. As will be appreciated, the diaper 10 and specifically the chassis 12 can be of various appropriate suitable shapes as are also known in the art. For example, the chassis 12 may have an overall rectangular shape, T-shape or an approximately hourglass shape. In the illustrated embodiment, the diaper absorbent article 10 and the chassis 12 have a longitudinal direction 14, with a longitudinal centerline 16 and a lateral direction 20, with a lateral centerline 22.

The diaper 10 generally defines a front waist section or area 24, a rear waist section or area 26, an intermediate section 30 which interconnects the front and rear waist sections, first and second opposed longitudinal sides, 32 and 34, respectively, and first and second opposed lateral ends 36 and 40, respectively. The first lateral end 36 is associated with the front waist section 24 and forms a front edge 41. Similarly, the second lateral end 40 is associated with the rear waist section 26 and forms a rear or back edge 42.

The front and rear waist sections 24 and 26, respectively, include the general portions of the article which are constructed to extend substantially over the front and rear abdominal regions, respectively, of a wearer during the use of the article 10. The intermediate section 30 of the article includes the general portion of the article which is constructed to extend over and about the crotch area or region, between the legs, of the wearer. The opposed sides 32 and 34 each contain a curved cut-out leg opening for the diaper 10 to more closely fit the legs of the wearer. The opposed ends 36 and 40 generally define a waist opening for the diaper 10 and typically are straight but may also be curvilinear.

The diaper chassis 12 may be of any suitable form or construction and generally does not form a limitation to the broader practice of the present invention. For example, as identified above for typical diaper products and as specifically shown in FIGS. 3 and 4, the diaper chassis 12 includes a substantially liquid impermeable backsheet 43, a porous, liquid permeable topsheet 44 positioned in facing relation with the backsheet 43, and an absorbent body or core such as an absorbent pad 45, which is located between the backsheet and the topsheet.

The diaper absorbent article 10 includes a suitable fastening system, such as generally designated by the reference numeral 48, employable to secure the diaper 10 about the waist of a wearer. In particular, the fastening system 48 includes first and second attachment flaps or ears 50 and 52, respectively. Each of the attachment ears 50 and 52 is suitably joined or attached to or with the chassis 12 such as at or about the rear waist section 26. For example, such joinder or attachment can be variously effected such as by means of either or both ultrasonic and adhesive bonding, generally designated by the reference numeral 54.

The attachment ears 50 and 52 each generally include a substrate 56 and a fastener 58. Suitable fasteners 58 may include hook-and-loop type fasteners, adhesive tape fasteners, buttons, pins, snaps, mushroom-and-loop fasteners and the like as may be desired for particular applications.

The diaper absorbent article 10 also advantageously includes, in accordance with a preferred embodiment of the invention, a containment liner assembly, generally designated by the reference numeral 60. As will be appreciated and described in greater detail below, such a containment liner assembly 60 may serve to more efficiently or effectively isolate at least certain bodily exudates, such as fecal matter, from the skin of a wearer.

Figure 2:
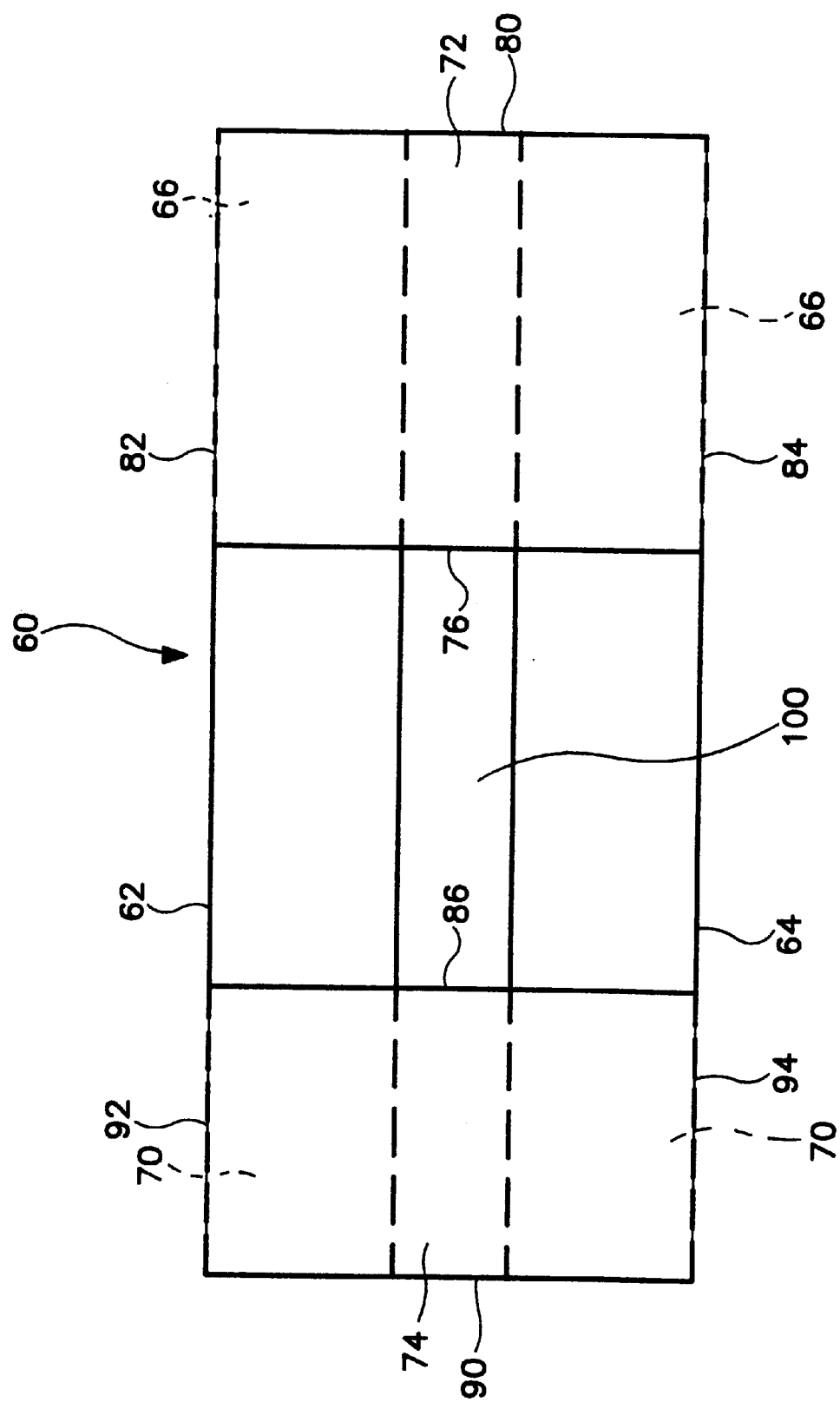
FIG. 2 is a top plan view of a containment liner assembly in accordance with one embodiment of the invention and such as used in the disposable diaper absorbent article shown in FIG. 1, also shown in a flat-out, uncontracted state (i.e., with all elastic induced gathering and contraction removed).

Turning to FIG. 2, the containment liner assembly 60 will be more specifically described. The containment liner assembly 60 generally includes first and second elongated elasticized members, 62 and 64, respectively. Such elasticized members may be formed or constructed of various suitable elastic materials such as known in the art for use as leg elastics in diaper absorbent articles. For example, such elastic members may comprise a single strand of elastic material or may comprise a plurality of parallel or nonparallel strands of elastic material. Where multiple strands are employed, the individual strands may be constructed to provide or supply substantially equal elastic forces or different elastic forces, as may be desired for particular absorbent article designs. For example, individual strands may be constructed of different diameter or other size parameter, or may be configured with different amounts of elongation to thereby provide a gradient or other variation of elastic tensions. Where the strands are nonparallel, two or more of the strands, may intersect or otherwise interconnect within the particular elastic member.

Each of the first and second elongated elasticized members, 62 and 64, has opposed first and second end portions, 66 and 70, respectively. Further, the first and second elongated elasticized members 62 and 64 of the assembly 60 are typically desirably spaced apart in general parallel elongated arrangement.

The assembly 60 also includes first and second containment liner members, 72 and 74, respectively. In the illustrated embodiment, the first containment liner member 72 is designed to be positioned and secured adjacent to the interior of the front waist section of the chassis 12 and is thus sometimes referred to herein as a "front" containment liner member. Correspondingly, the second containment liner member 74 is designed to be positioned and secured adjacent to the interior of the rear waist section of the chassis 12 and is thus sometimes referred to herein as a "back" or "rear" containment liner member.

Such front and back containment liner members 72 and 74, respectively, need not and preferably, in at least certain preferred embodiments, are not of the same dimensions or sizes. As will be appreciated and as shown in FIG. 1, it may be desirable to use a larger-sized containment liner member 72 in association with the front waist section 24 of the diaper 10 and a smaller-sized containment liner member 74 in association with the rear waist section 26 of the diaper 10.

The containment liner members 72 and 74 suitably preferably present a body-facing surface which is compliant, soft-feeling, and nonirritating to the skin of the wearer. As will be described in greater detail below, such containment liner members serve to form a barrier between solid waste exudates contained therebehind and the skin of the wearer. Thus, such containment liner members may be formed or fabricated of any material suitable for such purposes as will be apparent to those skilled in the art and guided by the teachings herein provided. For example, such liner members may typically be fabricated of a material less hydrophilic than the absorbent body, to present a relatively dry surface to the wearer, and may be sufficiently porous to be liquid permeable, permitting liquid to readily penetrate through the thickness thereof. Suitable containment liner members may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The liner members may also be suitably employed to help isolate the wearer's skin from liquids held in the absorbent body.

Various woven and nonwoven fabrics can be used for containment liner members in accordance with the invention. For example, such containment liner members may be composed of a meltblown or spunbonded web of polyolefin fibers.

Containment liner members may also be a bonded-carded web composed of natural and/or synthetic fibers. Containment liner members may be composed of a substantially hydrophobic material, and the hydrophobic material may, optionally, be treated with a surfactant or otherwise processed to impart a desired level of wettability and hydrophilicity. In a particular embodiment of the present invention, containment liner members comprise a nonwoven, spunbond, polypropylene fabric composed of about 2.8–3.2 denier fibers formed into a web having a basis weight of about 22 grams per square meter and a density of about 0.06 gram per cubic centimeter. Such containment liner members may be surface treated with an effective amount of a surfactant, such as about 0.3 weight percent of a surfactant commercially available from Hodgson Textile Chemicals Co. under the trade designation AHCOVEL BASE N-62.

Each of the first and second containment liner members, 72 and 74, is generally rectangular is shape. More specifically, the containment liner member 72 has an inner lateral end 76 and an opposed outer lateral end 80 as well as opposed first and second longitudinal edges 82 and 84. Similarly, the containment liner member 74 has an inner lateral end 86 and an opposed outer lateral end 90 as well as opposed first and second longitudinal edges 92 and 94.

In practice, such front and back liner members 72 and 74 are each respectively generally joined or attached to elasticized members 62 and 64 at about 0.75 inches and, most preferably, at about 0.0 to about 0.25 inches, from the respective edges 82 and 84 and 92 and 94.

Such liner members and elasticized members may be joined or attached using various appropriate techniques such as including, for example, ultrasonic bonding, heat and pressure sealing using a selected bonding pattern or adhesive bonding with a selected pattern of hotmelt or other type of adhesive. Thus, it is to be understood that the broader practice of the invention is not limited to a particular method or technique used to effect the joinder or attachment of a liner member with one or more elasticized members.

The containment liner assembly 60 includes a central or center portion, generally designated by the reference numeral 100, which is free of containment liner member material. The presence and use of such a containment liner assembly 60, having such a containment liner-free central portion 100, in a diaper absorbent article in accordance with the invention will be described in greater detail below making reference again to FIGS. 1, 3 and 4.

As shown in the figures, the containment liner assembly 60 is appropriately positioned and placed relative to the chassis 12 and then bonded, joined or otherwise appropriately attached thereto such as via adhesive bonding 102. For example, such joinder or attachment can be effected by joining the first and second elongated elasticized members 62 and 64, respectively, to a corresponding or associated chassis longitudinal side 32 and 34, respectively. In accordance with one preferred aspect of the invention, such joinder is done in fashion wherein the first end portion 66 of the first elongated elasticized member 62 is coterminous with the front edge 41 while the second end portion 70 of the first elongated elasticized member 62 is coterminous with the back or rear edge 42. Similarly, the first end portion 66 of the second elongated elasticized member 64 is coterminous with the front edge 41 while the second end portion 70 of the second elongated elasticized member 64 is coterminous with the back or rear edge 42.

As will be appreciated, in the diaper 10, the first and second elongated elasticized members 62 and 64 desirably serve to place and maintain at least one and preferably both the front and rear containment liner members 72 and 74 in body contact with the wearer while the diaper 10 is being normally worn, such as may serve to create a form of a seal between the inner or lead edge 76 and 86 of the liner members 72 and 74, respectively, and the body of the wearer and such as may serve to prevent of minimize the passage of solid waste exudates therebetween and thus serve to avoid or minimize extensive contact of the skin of the wearer by or with such bodily exudates.

For example, and as shown in FIG. 1 relative to the elongated elasticized member 64, such member may comprise several strands of LYCRA spandex which is available from E. I. DuPont de Nemours, a business having offices in Wilmington, Del. Such strands are individually designated by the reference numeral 110.

The containment liner assembly 60 may be joined or attached with the chassis 12 using various appropriate techniques such as including, for example, ultrasonic bonding, heat and pressure sealing using a selected bonding pattern or adhesive bonding with a selected pattern of hotmelt or other type of adhesive, such as described above.

As will be appreciated, in the use of the diaper absorbent article 10, the containment liner-free central portion 100 serves to form or create a pocket which has an opening passage wherethrough solid waste substances, such as excrement, may migrate while the front and rear containment liner members desirably remain adjacent or in contact with the body of the wearer such that further or other contact of the skin of the wearer by or with such solid waste materials is reduced or preferably avoided.

For example, as shown in FIGS. 3 and 4 relative to the liner member 72, an opening 114 is formed or created wherethrough such solid wastes can be passed into a containment volume or void area 116 formed or created between the liner member 72 and the diaper chassis 12, adjacent the front edge 41. As will be appreciated and as shown in FIG. 1, the liner member 74 and the diaper chassis 12 similarly cooperate to create or form a containment volume or void area, designated by the reference numeral 118, adjacent the rear edge 42.

While the invention has been described above with reference to containment liner assemblies and corresponding absorbent articles which include both a front waist containment liner member and a rear waist containment liner member, it is to be understood that the broader practice of the invention is not necessarily so limited. For example, if desired, the invention can be practiced in a form wherein only a front or a rear waist containment liner member is utilized. It will be appreciated, however, that in embodiment utilizing only a front or rear waist containment liner member without the other may have associated therewith a concomitant reduction is the efficacy in reducing or avoiding contact of the skin of the wearer by or with the associated solid waste materials.

While the broader practice of the invention is not limited to the use of components having a particular absolute or relative size, the use of components within certain relative size ratios has, at least initially, been found helpful in better ensuring desired operation and function of the such containment assemblies and associated absorbent articles, in accordance with the invention. For example, it has been found generally desirable in accordance with certain preferred practices of the invention to utilize a front waist section containment liner member having a longitudinal length ($L_f$) which is in the range of about 10 to about 50 percent, preferably in the range of about 25 to about 45 percent and, most preferably, in the range of about 35 to about 40 percent of the longitudinal length of the chassis ($L_c$) and a rear waist section containment liner member having a longitudinal length ($L_r$) which is in the range of about 10 to about 35 percent, preferably in the range of about 15 to about 30 percent and, most preferably, in the range of about 20 to about 30 percent of the longitudinal length of the chassis ($L_c$).

The containment liner assembly described above generally provides a larger containment volume for use in the containment of waste materials, such as fecal matter, than is normally obtainable or realizable with diaper absorbent articles which incorporate conventional or common elasticized hole liner designs. Further, the assembly process described above and such as may be used in association with the subject containment liner assembly and associated absorbent articles is generally simpler and more easily and efficiently conducted than those products which incorporate conventional or common elasticized hole liner designs. For example, the subject invention eliminates or otherwise avoids the need to cut a hole in a material web for use in the articles being manufactured.

Thus, the invention desirably provides absorbent articles of improved efficacy in avoiding or minimizing contact of the skin of the wearer by or with bodily exudates. Further, the invention generally provides absorbent articles which afford a containment space of sufficient volume to properly provide desired isolation of fecal matter while maintaining the designed for absorbency properties or characteristics of the article. Still further, the invention generally provides a containment liner assembly as well as corresponding absorbent articles and associated methods such as are desirably suited for large scale manufacture and production.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

We claim:

1. An absorbent article including a front waist area, forming a front edge, a back waist area forming a back edge, and a crotch area disposed between the front and back waist areas, the absorbent article having a chassis which includes an absorbent structure and a liquid permeable topsheet, the chassis having opposed first and second longitudinal sides and opposed first and second lateral sides, the absorbent article additionally comprising:

a first elongated elasticized member disposed along the first longitudinal side of the chassis, a second elongated elasticized member disposed along the second longitudinal side of the chassis, wherein each of the first and second elongated elasticized members having a first end portion coterminous with the back edge, and a first containment liner member having opposed first and second longitudinal ends and opposed inner and outer lateral ends with the first longitudinal end joined with the first elongated elasticized member first end portion and the second longitudinal end joined with the second elongated elasticized member first end portion, the first containment liner member forming a body-adjacent surface for a wearer, the first containment liner member at least in part spaced apart from the chassis to form an opening to a first containment volume formed between the first containment liner and the chassis, the first containment volume effective to isolate contents of the first containment volume from direct contact with a wearer, wherein each of the first and second elongated elasticized members have a second end portion opposite the first end portion with the second end portion coterminous with the front edge, the absorbent article additionally comprising a second containment liner member having opposed first and second ends with the second containment liner member first end joined with the first elongated elasticized member second end portion and the second containment liner member second end joined with the second elongated elasticized member second end portion.

2. The absorbent article of claim 1 wherein the first containment volume comprises a void defined at least in part by the first containment liner member and the chassis.

3. The absorbent article of claim 1 wherein the first containment volume is formed adjacent the back edge.

4. The absorbent article of claim 3 wherein the first containment liner member has a longitudinal length which is in the range of about 10 to about 35 percent of the longitudinal length of the chassis.

5. The absorbent article of claim 4 wherein the first containment liner member has a longitudinal length which is at least about 20 percent of the longitudinal length of the chassis.

6. The absorbent article of claim 1 wherein the second containment liner member and the chassis cooperate to form a second containment volume adjacent the front edge.

7. A containment liner assembly including a front waist area forming a front edge, a back waist area forming a back edge, and a crotch area disposed between the front and back waist areas, the absorbent article having a chassis which includes an absorbent structure and a liquid permeable topsheet, the chassis having opposed first and second longitudinal sides and opposed first and second lateral sides, a containment liner assembly comprising:

first and second elongated elasticized members adapted to be disposed along the first and second longitudinal sides of the chassis, respectively, with a first end portion of each of the first and second elongated elasticized members coterminous with the back edge, and a first containment liner member having opposed first ant second longitudinal ends and opposed inner and outer lateral ends with the first longitudinal end joined with the first elongated elasticized member first end portion and the second longitudinal end joined with the second elongated elasticized member first end portion, the first containment liner member forming a body-adjacent surface for a wearer, the first containment liner member at least in part spaced apart from the chassis to form an opening to a first containment volume formed between the first containment liner and the chassis, the first containment volume comprising a void defined at least in part by the first containment liner member and the chassis and effective to isolate contents of the first containment volume from direct contact with a wearer, wherein each of the first and second elongated elasticized members have a second end portion opposite the first end portion with the second end portions adapted to be coterminous with the front edge the containment liner assembly additionally comprising a second containment liner member having opposed first and second ends with the second containment liner member first end joined with the first elongated elasticized member second end portion and the second containment liner member second end joined with the second elongated elasticized member second end portion.

8. The containment liner assembly of claim 1 wherein the first containment liner member has a longitudinal length which is in the range of about 10 to about 35 percent of the longitudinal length of the chassis.

9. The containment liner assembly of claim 8 wherein the first containment liner member has a longitudinal length which is in the range of about 20 to about 30 percent of the longitudinal length of the chassis.

10. A method for providing a containment liner to an absorbent article having a front waist area forming a front edge, a back waist area forming a back edge, and a crotch area disposed between the front and back waist areas, the absorbent article having a chassis which includes an absorbent structure and a liquid permeable topsheet, the chassis having opposed first and second longitudinal sides and opposed first and second lateral sides, said method comprising:

forming a containment liner assembly by, joining a first end of a first containment liner member with a first end portion of a first elongated elasticized member, the first containment liner member forming a body-adjacent surface for a wearer, and joining an opposed second end of the first containment liner member with a first end portion of a second elongated elasticized member, and joining the containment liner assembly with the chassis by, joining the first elongated elasticized member along the first longitudinal side of the chassis such that the first end portion of the first elongated elasticized member is coterminous with the back edge and joining the second elongated elasticized member along the second longitudinal side of the chassis such that the first end portion of the second elongated elasticized member is also coterminous with the back edge with which the first end portion of the first elongated elasticized member is coterminous, wherein the first containment liner member at least in part is spaced apart from the chassis to form an opening to a first containment volume formed between the first containment liner and the chassis, the first containment volume effective to isolate contents of the first containment volume from direct contact with a wearer, and wherein said forming of a containment liner assembly additionally comprises;

joining a first end of a second containment liner member with a second end portion of a first elongated elasticized member, and joining an opposed second end of the second containment liner member with a second end portion of a second elongated elasticized member.

11. The method of claim 10 wherein said joining the containment liner assembly with the chassis additionally comprises:

joining the first elongated elasticized member along the first longitudinal side of the chassis such that the second end portion of the first elongated elasticized member is coterminous with the front edge and joining the second elongated elasticized member along the second longitudinal side of the chassis such that the second end portion of the second elongated elasticized member is also coterminous with the front edge.

12. The method of claim 10 wherein the first containment volume comprises a void defined at least in part by the first containment liner member and the chassis.

13. An absorbent article having a body-facing surface, the absorbent article including a front waist area forming a front edge, a back waist area forming a back edge, and a crotch area disposed between the front and back waist areas, the absorbent article having a chassis which includes an absorbent structure and a liquid permeable topsheet, the chassis having opposed first and second longitudinal sides and opposed first and second lateral sides, the absorbent article additionally comprising:

a first elongated elasticized member disposed along the first longitudinal side of the chassis, a second elongated elasticized member disposed along the second longitudinal side of the chassis, wherein each of the first and second elongated elasticized members having a first end portion coterminous with the front edge and a second end portion coterminous with the back edge;

a first containment liner member having opposed first and second ends with the first end joined with the first elongated elasticized member first end portion and the second end joined with the second elongated elasticized member first end portion, the first containment liner member at least in part forming a first portion the body-facing surface of the absorbent article, wherein the first containment liner member and the chassis cooperate to form a first containment volume therebetween adjacent the front edge and wherein the first containment liner member has a longitudinal length which is in the range of about 10 to about 50 percent of the longitudinal length of the chassis, and a second containment liner member having opposed first and second ends with the first end joined with the first elongated elasticized member second end portion and the second end joined with the second elongated elasticized member second end portion, the second containment liner member at least in part forming a second portion of the body-facing surface of the absorbent article, wherein the second containment liner member and the chassis cooperate to form a second containment volume therebetween adjacent the back edge and wherein the second containment liner member has a longitudinal length which is in the range of about 10 to about 35 percent of the longitudinal length of the chassis.

14. The absorbent article of claim 13 wherein the first containment volume comprises a first void defined at least in part by the first containment liner member and the chassis, the first containment volume effective to isolate contents of the first containment volume from direct contact with a wearer.

15. The absorbent article of claim 13 wherein the second containment volume comprises a second void defined at least in part by the second containment liner member and the chassis, the second containment volume effective to isolate contents of the second containment volume from direct contact with a wearer.

* * * * *